United States Patent [19]

Richards et al.

[11] Patent Number: 5,093,251

[45] Date of Patent: Mar. 3, 1992

[54] CASSETTE METHOD OF GENE SYNTHESIS

[75] Inventors: John H. Richards, Bradbury; Sheila A. Iverson, Pasadena; Dianne M. Perez, Sun Valley, all of Calif.

[73] Assignee: California Institute of Technology, Pasadena, Calif.

[21] Appl. No.: 866,780

[22] Filed: May 23, 1986

[51] Int. Cl.$^5$ .................. C12N 15/10; C12N 15/29; C12N 1/21

[52] U.S. Cl. .................. 435/172.3; 435/91; 435/252.3; 435/320.1; 536/27; 935/6; 935/8; 935/9; 935/16; 935/22; 935/59; 935/60; 935/61; 935/66; 935/72; 935/73

[58] Field of Search .......... 435/91, 70, 172.3, 252.3, 435/322.1; 935/9, 19; 536/27, 28, 29

[56] References Cited

FOREIGN PATENT DOCUMENTS 8304053 11/1983 PCT Int'l Appl. .

Primary Examiner—Richard C. Peet
Attorney, Agent, or Firm—Joseph Mueth

[57] ABSTRACT

The method of synthesizing a segment of DNA, typically a gene, of predetermined structure which comprises synthesizing a first pair of oligonucleotides having ends complementary to the ends enzymatically made at a restriction site on a standard plasmid vector, said first pair of oligonucleotides including adjacent their ends portions of said predetermined structure and each having a pair of restriction sites internal to said portions of predetermined structure which restriction sites are unique to the enzyme and not present in the plasmid vector, cloning said first pair of oligonucleotides into said standard plasmid vector, and amplifying said plasmid vector in vivo to recover plasmid vector containing said first pair of oligonucleotides, repeating said method with a second pair of ologonucleotides, containing portions of predetermined structure which are adjacent to the portions present in the first pair of oligonucleotides, and continuing said repetition until all of said segment of predetermined structure has been cloned into said standard vector and amplified.

10 Claims, 2 Drawing Sheets

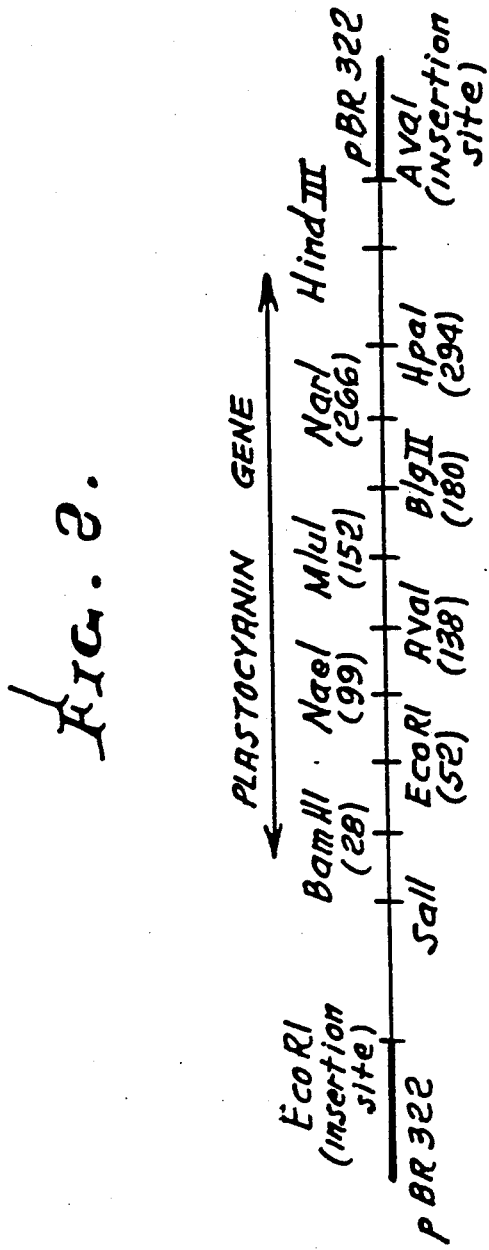

CASSETTE METHOD OF GENE SYNTHESIS

BACKGROUND OF THE INVENTION

The invention disclosed in this patent application was made in part under Office of Naval Research Contract No. N00014-83-K-0487.

Proteins act in biological systems in many ways; as catalysts, transport agents, hormones, cell surface receptors, electron carriers, antibodies and markers of individuality. In general, the study of protein function focuses on a protein that occurs naturally though some minor chemical modifications of the native proteins are possible. The molecular basis of function could be studied in much greater detail if one could vary at will the protein structure in order to test predictions that result from a hypothetical model of its action. These insights would also provide a rational basis for designing specific proteins, with novel and useful properties not previously available. For these reasons, the ability to generate a protein with any desired structure represents an important goal.

The amino acid sequence of a protein uniquely determines its three-dimensional structure and function. The amino acid sequence is, in turn, determined by the sequence of bases in the DNA of the structural gene that encodes the protein. In vitro mutagenesis techniques and methods for efficient oligodeoxyribonucleotide synthesis have been recently developed. These advances, along with other techniques of molecular biology, now allow the creation of a protein with any desired amino acid sequence. This process involves preparation of the appropriate gene, either by total synthesis or specific mutation of a naturally occurring gene, followed by expression of this gene in an appropriate microbiological host.

Various approaches to the synthesis of genes have been proposed. Genes consist of double-stranded DNA molecules, whose chemical structure is basically like that of a ladder. The two strands of DNA molecules adhere to one another because the units, called nucleotides, that make up the strands are mutually attracted to one another by their complementary chemical forms.

Over a period of some 20 years, a series of interactions between genetics, biochemistry and microbiology has led to the development of a new technology. This technology has made possible the transfer of a gene or a small cluster of genes, on a segment of DNA from almost any organism to one of the standard and easily grown laboratory organisms; the most conspicuous organism being the bacterium *Escherichia coli*. A host of supplementary techniques permit the regulation of the expression of the transferred genes so that the proteins they specify may be synthesized very efficiently in the bacterium. This allows the protein to be produced cheaply and abundantly. In order to produce desired proteins using this recombinant DNA technology, one must either isolate or synthesize the gene that encodes that particular protein.

The advantage of total synthesis is the opportunity to engineer desired features into the DNA such as: restriction sites, regulatory signals for transcription or translation, usage of the most abundant tRNA codons for a given organism. The first gene synthesis was carried out by Khorana and coworkers in the 1960s with the yeast alanine tRNA gene (Khorana, H. et al. (1971) Studies on polynucleotides: total synthesis of the structural gene for an alanine transfer ribonucleic acid from yeast. *J.Mol.Bio.* 72, 209-217 and accompanying papers.) The key concept in Khorana's work is the inherent ability of DNA to base pair. Also a major factor to his success was the discovery of DNA joining enzymes. Khorana formulated the following three step approach, Khorana, H. G. (1979) Total synthesis of a gene. *Science* 203, 614-625: (a) chemical synthesis of short oligodeoxynucleotides, (b) enzymatic phosphorylation of 5'OH endgroups to monitor joining, and (c) ligase-catalyzed joining of hydrogen bonded duplexes.

Several genes have since been synthesized using this approach, some examples of which are the following: In 1977, Riggs, Itakura and coworkers synthesized the gene for somatostatin, Itakura, K., Tadaaki, H., Crea, R., Riggs, A. D., Heyneker, H. L., Bolivar, F. and Boyer, H. W. (1977) Expression in Escherichia coli of a chemically synthesized gene for the hormone somatostatin *Science* 198, 1056-1063, and fused this to the gene for β-galactosidase in the plasmid pBR322, Bolivar, F., Rodriguez, R. L., Green, P.J., Betlach, M. C., Heyneker, H. L., Boyer, H. W. (1977) Construction and characterization of new cloning vehicles. II. A multipurpose cloning system. *Gene* 2, 93-113, Sutcliffe, J. C. (1978) Nucleotide sequence of the ampicillin resistance gene of Escherichia coli plasmid pBR322. *Proc. Natl. Acad. Sci. USA* 75, 3737-3741, Maniatis, T., Fritsh, E. F. and Sambrook, Jr. (1982) Molecular cloning: A laboratory manual. Cold Spring Harbor Laboratory, New York. This represents the first recovery of a functional polypeptide product from chemically synthesized DNA. The synthesis required for this project consisted of eight oligodeoxynucleotides with five base complementary overlaps for efficient oligodeoxynucleotide joining.

Two of the longest genes to be synthesized include human leukocyte interferon α-1, Edge, M. D., Greene, A. R., Gillian, H. R., Meacock, P. A., Schuch, W., Scanlon, D. B., Atkinson, T. C., Newton, C. R. and Markham, A. F. (1981) Total synthesis of a human leukocyte interferon gene. *Nature* 292, 756-762, which is 514 base pairs (166 amino acids) and bovine rhodopsin, Gerretti, L., Karnik, S. S., Khorana, H. G., Nassai, M. and Oprian, D. D. (1986) Total synthesis of a gene for bovine rhodopsin. *Proc. Natl. Acad. Sci. USA* 33, 599-603, which is 1057 base pairs (348 amino acids). These are sections of DNA which include initiation and termination codons and restriction enzyme sites for insertion into a plasmid. The synthesis for human leukocyte interferon α-1 requires 67 oligonucleotides with an average length of 15 nucleotide residues. The synthesis for bovine rhodopsin required 72 synthetic oligonucleotides with average lengths of 15–40 nucleotide residues An alternate approach was developed by Itakura, Rossi and coworkers for the synthesis of a 132 base pair segment coding for amino acids 126-stop of human leukocyte interferon α-2, Rossi, J. J., Kierzek, R., Huang, T., Walker, P. A. and Itakura, K. (1982) An alternate method for synthesis of double-standed DNA segments. *J. Biol Chem.* 257, 9226-9229. This method involves synthesis of oligonucleotides which are annealed to form partial duplex structures. These structures are then used as a substrate for DNA polymerase I (Klenow), McHenry, C. and Kornberg, A. (1977) DNA polymerase III holoenzyme of Escherichia coli: purification and resolution into subunits. *J. Mol. Biol.* 252, 6478-6484, and the four deoxynucleoside triphosphates. These segments are then digested with appropriate restriction endonucleases for insertion into the plasmid and the final step is blunt end ligation to close the plasmid. This approach reduces the number of synthetic oligonucleotides required, however, with the introduction of automated DNA synthesis this is no longer a major concern. Two of the most recent examples of synthetic genes are those which code for the human complement fragment $C_{5a}$ and Calmodulin, Roberts, D. M. Crea, R., Malecha, M., Alvarado-Urbina, G., Chiarello, R. H. and Watterson, D. M. (1985) Chemical synthesis and expression of a calmodulin gene designed for site-specific mutagenesis. *Biochemistry* 24, 5090–5098.

Chemists attempting to build long DNA molecules of hundreds of units have, until now, synthesized short stretches of singlestranded DNA that correspond to pieces of the "ladder rails." Each of these rails was designed so that it complemented an opposing segment, but with an extra piece extending beyond that segment. This extended piece complemented another extended piece of another pair of rails. When all the segments were mixed together, they tended to form into doublestranded DNA with the desired sequence. Once joined, the rails were stitched together using DNA-joining enzymes.

Using this puzzle-piece approach, genetic engineers have been able to join up to 14 such segments at once, before the level of misjoining became too high.

The present invention represents an enormously flexible, infinitely expandable, completely controllable approach to the design of new genes; it allows even beginners to easily build large DNA segments.

A new method to facilitate construction of long strands of DNA has been developed.

According to our invention, there has been developed a way of reliably building large genes chunk by chunk from the outside in. In this method, there is first joined a small stretch of the desired gene—comprising the beginning and end pieces—to a large circular piece of DNA called a vector or plasmid. Between these beginning and end pieces are "restriction sites" where the pieces can be cut apart using enzymes. Vectors are specially built pieces of DNA, widely used in genetic engineering, that can carry attached DNA into a living cell, where the cell can be induced to make many copies of the DNA. After using bacteria to make copies of the plasmid vector carrying the gene segment, the scientists extract the copies, and chemically snip the inserted DNA, separating the beginning and end pieces. Between these pieces, they insert another segment of the desired gene, representing the next inward two segments of the desired gene, with restriction sites between them. Once more the vector is inserted into bacteria to copy the resulting longer stretch of DNA. The process of cutting, inserting, and copying continues until the desired gene has been produced. There is no limit to the size of predetermined gene structure that this synthetic strategy will allow. Accordingly, it is to be anticipated that this invention will find important utilization by those skilled in this art.

SUMMARY OF THE INVENTION

Briefly, the present invention comprises the method of synthesizing a segment of DNA, typically a gene, of predetermined structure which comprises synthesizing a first pair of oligonucleotides having ends complementary to the ends enzymatically made at a restriction site on a standard plasmid vector, said first pair of oligonucleotides including adjacent their ends portions of said predetermined structure and each having a pair of restriction sites internal to said portions of predetermined structure which restriction sites are unique to the enzyme and not present in the plasmid vector, cloning said first pair of oligonucleotides into said standard plasmid vector, and amplifying said plasmid vector in vivo to recover plasmid vector containing said first pair of oligonucleotides, repeating said method with a second pair of oligonucleotides, containing portions of predetermined structure which are adjacent to the portions present in the first pair of oligonucleotides, and continuing said repetition until all of said segment of predetermined structure has been cloned into said standard vector and amplified.

It is an object of our invention to provide a novel method for the synthesis of long DNA sequences including genes.

It is a further object of this invention to provide a method of synthesizing genes using cloning and in vivo amplification.

It is a major object of our invention to provide a means for a more precise synthesis of longer segments of DNA.

These and other objects and advantages of our invention will be apparent to those skilled in the art from the more detailed description which follows.

BRIEF DESCRIPTION OF THE DRAWINGS

FIG. 2 is a restriction map of the poplar leaf plastocyanin gene.

DESCRIPTION OF PREFERRED EMBODIMENTS

Figure 1:
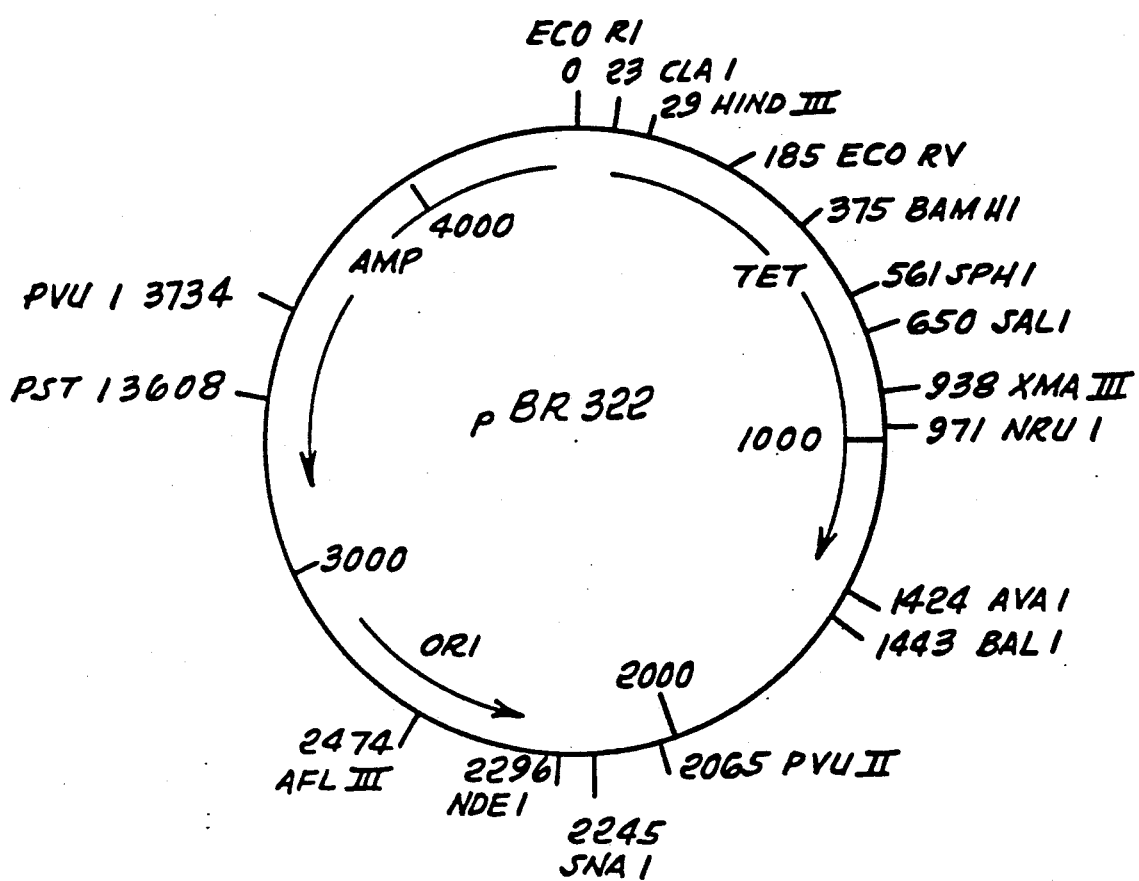
FIG. 1 is a restriction map of pBR322 DNA. Size: 4.3 kb; selection markers: $Amp^r$, $Tet^r$, single sites: Ava I, Pst I, Bom MI, Pvu II, Cla I, Sol I, Eco RI, Hind III.

The synthesis proceeds step by step to produce a gene encoding the desired sequence of amino acids and having the decided advantage over a natural gene of incorporating many unique restriction sites that will greatly facilitate further manipulations. The synthesis of the requisite oligonucleotides (a total of about 1300 bases) for each step requires about 150 hours of machine time on a three column DNA synthesizer (Applied Biosystems, Inc., Foster City, Calif.).

The present invention involves the synthesis of segments of the gene on the machine using known procedures; these segments are cloned at intermediate stages into an appropriate vector, such as pBR322, which then allows amplification of the gene at intermediate stages. The construction of the gene proceeds from the ends towards the middle. Thus, after a segment has been cloned into the vector and amplified, the vector, with the cloned segment that includes internal restriction sites, can then be opened at these sites which in turn act as recipient sites for additional segments of the structural gene in subsequent steps.

To illustrate the general strategy, assume that the structural gene will contain segments aAbBcCdDeEfFg; the boundary (for example, a, b, c, d . . . ) between the segments (for example, A, B, C, D . . . ) defines a restriction site unique to the enzyme and not present in the vector.

In the case illustrated, a is a unique restriction site that will joint the 5' end of the sense strand of the synthetic DNA into the vector, b is a unique restriction site within the structural gene that joins segments A and B, g is a restriction site that will join the 3' end of the gene into the vector.

In the first "step" of the synthesis one prepares an oligonucleotide aAbxxxfFg that can be inserted between sites a and g in the vector. The x's between b and f indicate random bases that allow opening of the intermediate by restriction enzymes at both sites b and f.

Step I 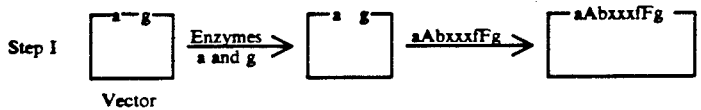

Vector

To receive an additional segment b-B-c-xxx-eE-f in "step" II.

Step II 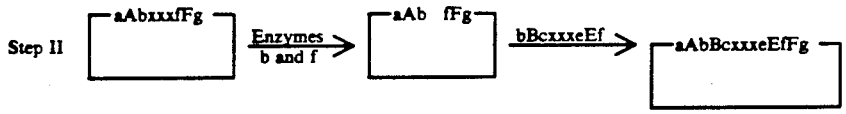

In "step" III, the final segments can be added to complete the synthesis.

Step III 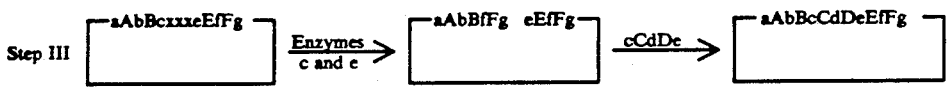

The segments were prepared by synthesis of four oligonucleotides that were assembled in the normal manner with cohesive ends to direct the assembly. For example,

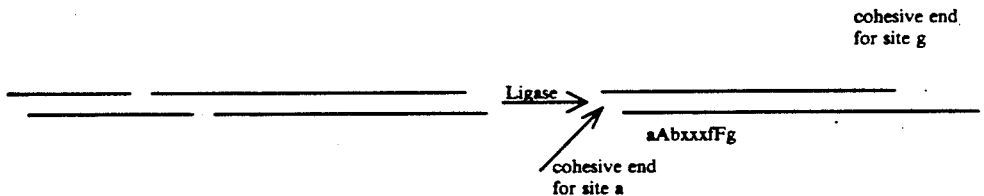

In previously reported synthesis of genes, more than four fragments have been assembled into a defined sequence taking advantage of the specificity of hybridization inherent in cohesive ends of uniquely complementary sequences. There is an upper limit to the number of fragments that can be cleanly and specifically linked thereby setting a maximum size for a gene that can be prepared by such assembly of all fragments at one time. The strategy of our invention allows, in principle, the synthesis of a gene of any size. Also, one can amplify the vector containing inserted segments of gene after each step and also check at such an intermediate stage that the correct sequence is present before proceeding; in this sense such a strategy allows editing during the course of synthesis.

As outlined above, this invention using this strategy is relatively conservative; each "step" incorporates about 100–120 bases of the eventual gene. However, greater overall speed can be achieved by ligating six (or even eight) fragments before insertion into the vector thereby increasing to 150–200 (or even 200–250) the number of bases that can be introduced per "step." We are currently using this technique for the construction of genes encoding the blue copper proteins azurin and plastocyanin with great ease and success. After synthesis and purification of the requisite oligonucleotides, our experience suggests that the manipulation of each "step" requires 3–5 days.

The vector we used for the construction is pBR322. The growing gene is cloned between the EcoRI and AvaI sites, thereby eliminating the DNA normally present between these two sites and losing the tetracycline resistance. This procedure retains the $Amp^R$ and so provides a suitable marker for selection. In cloning at the AvaI site used for insertion, we destroy the AvaI site and, for this reason have inserted a BglII site at the 3' end of the sense strand. Both the EcoRI and BglII sites are just outside the structural gene.

The following Example will serve to illustrate our invention, and is not limiting in any way.

EXAMPLE

The protein considered is the blue copper protein, plastocyanin, which is responsible for essential redox processes in many plants (involving one electron oxidation-reduction of the copper). The objective of this project is to prepare structural variants of plastocyanin to study the origin of the particular, and unusual nature of the oxidation-reduction behavior of blue copper proteins.

STRATEGY FOR CONSTRUCTION OF A GENE FOR PLASTOCYANIN

The synthesis of a gene encoding the amino acid sequence of the blue cooper protein plastocyanin employs several steps. The strategy for construction of the plastocyanin gene is outlined below.

1. The DNA sequence was obtained from the known 99 amino acid sequence for poplar leaf plastocyanin, Clothia, C. and Lesk, A. M., (1982), *J. Mol. Biol.* 160, 309–323.

2. Restriction site search. These sites must be unique to the completed gene as they are necessary for construction of the gene and are shown below.

3. Homology search on oligonucleotides to avoid self-complementary sequences or complementary regions with other oligodeoxynucleotides other than those intended for the formation of partial duplex structures.

4. Four "step" construction of the gene (to be discussed in detail).

The synthetic gene uses those codons preferred by E. coli wherever possible, although some changes are required to introduce restriction sites and/or to reduce homologous sequences. E. coli is used as the host for expression. The vector is pBR322 in which the gene is being introduced between the Eco RI and Ava I sites.

The strategy for producing the synthetic gene involves construction of the gene from both ends toward the middle with the use of restriction sites appropriate to the structural gene for poplar leaf plastocyanin as places for inserting newly synthesized elements of the gene. Each step involves chemical synthesis of two pairs of oligonucleotides followed by in vitro enzymatic manipulations. The products of these in vitro steps are transform E. coli for the purpose of amplifying the amount of plasmid. About 80-100 base pairs are introduced in each step. In a subsequent step, restriction sites specifically incorporated in the previous step are opened and serve as places for insertion of new DNA. The gene for plastocyanin, 297 base pairs, is synthesized in four such steps. The plasmid is then amplified in vivo in E. coli. Cloning the new DNA between the Eco RI site (A) and the Ava I site (Z) in pBR322 leaves the gene for β-lactamase intact and thereby allows selection for ampicillin resistance.

Step I inserts DNA between the Eco RI and AvaI sites of pBR322 in the process destroying these two recognition sites. To compensate, and for subsequent easy manipulation of the structural gene, a SalI site is created just before the initiation ATG codon and similarly a HindIII site is created just after the TAG termination codon. The newly inerted DNA includes an Eco RI site (not the original Eco RI site in pBR322) and a HindIII site. In step II, the DNA is opened at these sites (Eco RI and HindIII, B and Y in the previous example) and the new DNA is inserted. This new DNA contains an AvaI site (not the original AvaI site in pBR322) and a HindIII site. In step III, the DNA is opened at the AvaI and HindIII sites and new DNA is inserted that contains BglII and NarI sites. In step IV, the DNA is opened at the BglII and NarI sites and the final DNA is inserted. After each step, the plasmid intermediate is amplified in E. coli. The ampicillin resistance conferred by the intact β-lactamase gene of the plasmid is used for positive selection.

Step I a. Synthesize oligodeoxynucleotides IAT,IAB,IBT and IBB. b. Kinase 5' ends and hybridize. c. Digest pBR322 with Eco RI followed by Ava I. d. Ligate fragments to form new plasmid. e. Use plasmid to transform E. coli, grow transformed E. coli cells and isolate plasmid.

Step II a. Synthesize oligodeoxynucleotides IIAT,IIAB,IIBT and IIBB. b. Kinase 5' ends and hybridize. c. Digest plasmid from step Ie with Eco RI and Hind III. d. Ligate fragments to form new plasmid. e. Use plasmid to transform E. coli, grown transformed E. coli cells and isolate plasmid.

Step III a. Synthesize oligodeoxynucleotides IIAT,IIAB,IIIBT and IIIBB. b. Kinase 5' ends and hybridize. c. Digest plasmid from IIe with Ava I followed by Hind III. d. Ligate fragments to form new plasmid. e. Use plasmid to transform E. coli, grow transformed E. coli cells and isolate plasmid.

Step IV a. Synthesize oligodeoxynucleotides IVAT,IVAB,IVBT and IVBB. b. Kinase 5' ends and hybridize. c. Digest plasmid from IIIe with Bgl II followed by Nar I. d. Ligate fragments to form final plasmid. e. Use plasmid to transform E. coli, grow transformed E. coli cells and isolate plasmid.

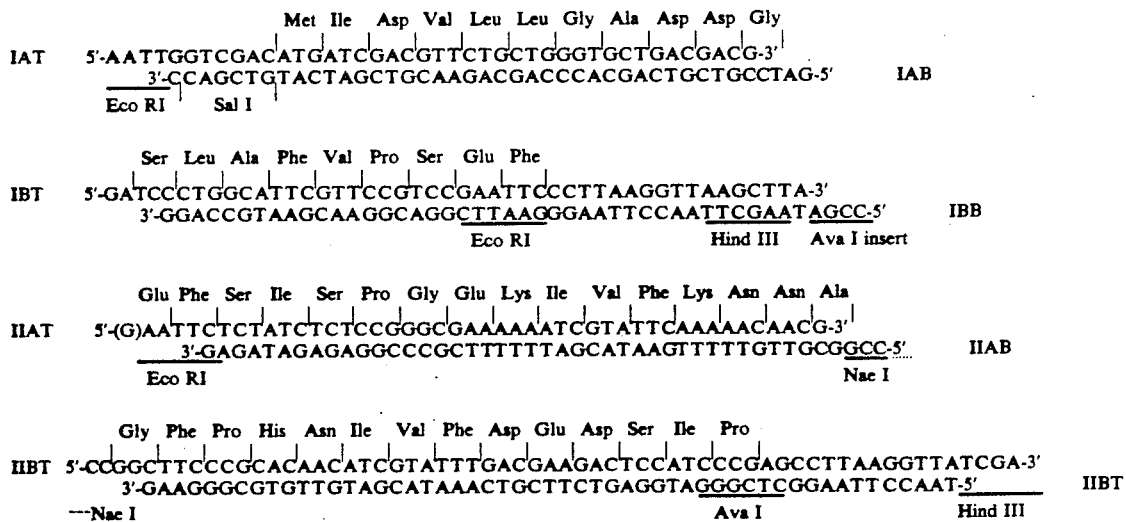

Construction of the gene for poplar leaf plastocyanin. Synthetic oligodeoxynucleotides for step 1 and step 2 oligodeoxynucleotides designed with correct overhangs for ligation into the plasmid digested with the appropriate restriction endonucleases.

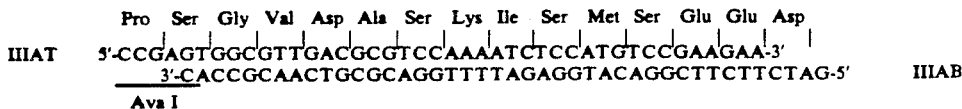

```
                    Gly  Ala  Gly  Met  Val  Gly  Lys  Val  Thr  Val  Asn  Trm
IIIBT   5'-GATCTCCTTAAGGTTGGCGCCGGTATGGTTGGTAAAGTAACCGTTAACTAGA-3'
            3'-AGGAATTCCAACCGCGGCCATACCAACCATTTCATTGGCAATTGATCTTCGA-5'        IIIBB
           Bgl II       Nar I                                        Hind III Asp  Leu  Leu  Asn  Ala  Lys  Gly  Glu  Thr  Phe  Glu  Val  Ala  Leu  Ser
IVAT    5'-GATCTGCTGAACGCAAAAGGTGAAACTTTTGAAGTAGCACTG-3'
            3'-ACGACTTGCGTTTTCCACTTTGAAAACTTCATCGTGACAGGT-5'         IVAB
           Bgl II Ser  Asn  Lys  Gly  Glu  Tyr  Ser  Phe  Tyr  Cys  Ser  Pro  His  Gln  Gly
IVBT    5'-TCCAACAAAGGTGAATACTCCTTCTACTGCTCCCCGCACCAGGG-3'
              3'-TGTTTCCACTTATGAGGAAGATGACGAGGGGCGTGGTCCCGC-5'         IVBB
                                                           Nar I
```

Construction of the gene for poplar leaf plastocyanin. Synthetic oligodeoxynucleotides for step 3 and step 4 oligodeoxynucleotides designed with correct overhangs for ligation into the plasmid digested with the appropriate restriction endonucleases.

Having fully described the invention, it is intended that it be limited only by the lawful scope of the appended claims.

We claim:

1. The method of synthesizing a segment of DNA of predetermined known structure which comprises:
    (1) obtaining a first pair of oligonucleotides having ends complementary to the ends made by restriction enzyme cleavage at a restriction site on a plasmid vector, said first pair of oligonucleotides including adjacent at least one of their ends, portions of said segment of DNA of predetermined known structure and each having a pair of restriction sites internal to said portions of said segment of DNA of predetermined known structure which restriction sites are unique to the enzyme and not present in the plasmid vector,
    (2) cloning said first pair of oligonucleotides into said plasmid vector,
    (3) amplifying said plasmid vector in vivo to recover plasmid vector containing said first pair of oligonucleotides,
    (4) repeating steps (1) to (3) with a second pair of oligonucleotides, containing portions of said segment of DNA of predetermined known structure which are adjacent to the portions present in the first pair of oligonucleotides, and
    (5) continuing said repetition until all of said segment of DNA of predetermined known structure has been cloned into said vector and amplified.

2. The method of claim 1 wherein said segment is a gene.

3. The method of claim 1 wherein said plasmid vector is amplified using bacteria in vivo to recover plasmid vector in steps (3) to (5).

4. The method of claim 3 wherein said plasmid vector is amplified using *E. coli*.

5. The method of claim 1 wherein about 80 to 100 base pairs are present in the oligonucleotides used in each step.

6. The method of claim 1 wherein the predetermined structure is the gene for plastocyanin having 297 base pairs.

7. The method of claim 1 wherein the gene of predetermined structure is obtained in four steps.

8. The method of claim 1 wherein each of said pairs of oligonucleotides is synthesized on a DNA synthesizer.

9. The method of claim 1 wherein plasmid vector pBR322 is enzymatically cut in the first step between the EcoRI and AvaI sites, and the said first portion is inserted therein.

10. The method of claim 1 wherein the plasmid after the first step and all subsequent steps is ampicillin resistant and such resistance provides positive selection.

* * * * *